(12) United States Patent
Sleevi et al.

(10) Patent No.: US 7,968,679 B2
(45) Date of Patent: Jun. 28, 2011

(54) PURIFIED RHIGF-I/RHIGFBP-3 COMPLEXES AND THEIR METHOD OF MANUFACTURE

(75) Inventors: Mark C. Sleevi, Midlothian, VA (US); Glen L. Kelley, Glen Allen, VA (US)

(73) Assignee: Insmed Incorporated, Glen Allen, VA (US)

( * ) Notice: Subject to any disclaimer, the term of this patent is extended or adjusted under 35 U.S.C. 154(b) by 27 days.

(21) Appl. No.: 11/311,633

(22) Filed: Dec. 20, 2005

(65) Prior Publication Data

US 2006/0166884 A1 Jul. 27, 2006

Related U.S. Application Data

(60) Provisional application No. 60/639,349, filed on Dec. 24, 2004.

(51) Int. Cl.
- *A61K 38/00* (2006.01)
- *A61K 38/30* (2006.01)
- *C07K 14/435* (2006.01)
- *C07K 14/65* (2006.01)

(52) U.S. Cl. ............ 530/350; 514/8.5; 514/8.6; 514/8.7

(58) Field of Classification Search .................. None
See application file for complete search history.

(56) References Cited

U.S. PATENT DOCUMENTS

| | | | |
|---|---|---|---|
| 5,200,509 A | 4/1993 | Spencer et al. | |
| 5,670,341 A | 9/1997 | Spencer et al. | |
| 5,681,818 A | 10/1997 | Spencer et al. | |
| 5,723,441 A | 3/1998 | Higley et al. | |
| 5,789,547 A | 8/1998 | Sommer et al. | |
| 5,948,757 A | 9/1999 | Sommer et al. | |
| 6,015,786 A | 1/2000 | Mascarenhas et al. | |
| 6,017,885 A | 1/2000 | Basi et al. | |
| 6,025,332 A | 2/2000 | Mascarenhas | |
| 6,025,368 A | 2/2000 | Mascarenhas et al. | |
| 6,417,330 B1 | 7/2002 | Mascarenhas et al. | |
| 6,436,897 B2 * | 8/2002 | Danko et al. ............ | 514/2 |
| 6,514,937 B1 | 2/2003 | Mascarenhas | |
| 6,518,238 B1 | 2/2003 | Mascarenhas | |
| 2002/0004478 A1 * | 1/2002 | Danko et al. ............ | 514/2 |
| 2003/0087806 A1 * | 5/2003 | Danko et al. ............ | 514/2 |

FOREIGN PATENT DOCUMENTS

| | | |
|---|---|---|
| DE | 199 51 824 A1 | 5/2001 |
| WO | WO 95/03817 A1 | 2/1995 |
| WO | WO 99/32620 A1 | 7/1999 |
| WO | WO 02/24219 A1 | 3/2002 |

OTHER PUBLICATIONS

Yoshimura et al., J Immunol. 1989; 142: 1956-1962.*
Patten et al., (Dev Biol (Basel). 2003; 112: 81-97.*
Chi et al., Pharmaceutical Res. 2003; 20: 1325-1336.*
Adams et al., "Pharmacokinetics and Bioavailability of rhIGF-I/IGFBP-3 in the Rat and Monkey," *Progress. Growth Factor Res.* 6(2-4):347-56 (1995).
Blum et al., "Plasma IGFBP-3 Levels as Clinical Indicators," *Modern Concepts of Insulin-like Growth Factors*, pp. 381-393, 1991.
Geoghegan et al,. "Spontaneous α-N-6-phospyhogluconoylation of a "His Tag" in *Escherichi coli*: The Cause of Extra Mass of 258 or 178 Da in Fusion Proteins," *Analytical Biochemistry* 267(1) 169-84, 1999.

* cited by examiner

*Primary Examiner* — Bridget E Bunner
*Assistant Examiner* — Christina Borgeest
(74) *Attorney, Agent, or Firm* — Greenberg Traurig, LLP

(57) ABSTRACT

Complexes of IGF-I and IGFBP-3 with new levels of purity are provided. Chromatographic techniques have been developed that remove contaminants, such as mass and charge variants of IGFBP-3. The new techniques enable the production of high-quality pharmaceutical compositions comprising IGF-I/IGFBP-3 complexes.

10 Claims, 6 Drawing Sheets

US 7,968,679 B2

PURIFIED RHIGF-I/RHIGFBP-3 COMPLEXES AND THEIR METHOD OF MANUFACTURE

BACKGROUND

1. Field of the Invention

The present invention relates to compositions comprising ultra-pure complexes of insulin-like growth factor I and insulin like growth factor binding protein-3, and methods of making the same.

2. Description of the Related Art

IGF-I/IGFBP-3 is a protein complex of insulin-like growth factor-I ("IGF-I") and insulin like growth factor binding protein-3 ("IGFBP-3"). IGF-I is a small polypeptide with strong structural and functional homology to pro-insulin. As such, IGF-I elicits many of the physiological effects of insulin.

IGF-I/IGFBP-3 complexes may be used for the treatment of a wide array of disorders (See, e.g., U.S. Pat. Nos. 5,681,818, 5,723,441, 5,948,757, 6,015,786, 6,017,885, 6,025,332, 6,025,368, 6,514,937, and 6,518,238). In healthy individuals, IGF-I can be found within the blood circulation bound by other proteins. For example, IGF-I is frequently bound to IGFBP-3, the most abundant IGF-I binding protein. The IGF-I/IGFBP-3 complex associates with and an acid-liable subunit protein, forming a 150 kD complex. See Adams et al., *Prog. Growth Factor Res.* 6(2-4):347-56 (1995). This large ternary complex serves as a circulatory reservoir of IGF-I as IGF-I/IGFBP-3 complexes exhibit a longer half-life and improved stability as compared to free IGF-I. See Adams et al., supra, and Blum et al. (1991), Plasma IGFBP-3 Levels as Clinical Indicators, in *Modern Concepts of Insulin-like Growth Factors*, pp. 381-93, E. M. Spencer, ed., Elsevier, N.Y.

IGF-I, IGFBP-3, and IGF-I/IGFBP-3 complexes can be obtained from natural sources or by recombinant techniques. Recombinant technology can be used to produce IGF-I, IGFBP-3, and IGF-I/IGFBP-3 complexes in eukaryotic and prokaryotic organisms (See, e.g., U.S. Pat. Nos. 5,200,509, 5,670,341, 5,789,547, and 6,417,330). Recombinant IGF-I, IGFBP-3, and IGF-I/IGFBP-3 complexes can be cultured in batch or continuous formats, with the harvesting of either the cell culture supernatant or the recombinant cells themselves.

IGF-I, IGFBP-3, and IGF-I/IGFBP-3 complexes typically are purified after expression in recombinant systems using such techniques as size exclusion chromatography, hydrophobic interaction chromatography, and ion exchange chromatography. However, such techniques fail to remove all impurities. For example, IGF-I/IGFBP-3 complexes typically are present in partially purified preparations containing protein aggregates. Moreover, new impurities, such as mass and charge variants of IGFBP-3, have been discovered that are not removed by prior art techniques. FIG. 1 provides a cation exchange trace obtained from the linear gradient carboxymethyl ion exchange ("CM-IEX") chromatography of samples comprising IGF-I/IFGBP-3 complexes and protein aggregates. FIG. 2 provides a LC/MS analysis of IGF-I/IGFBP-3 complexes purified using linear gradient CM-IEX showing newly discovered mass and charge variants.

It is well accepted in the Pharmaceutical arts that drug purity is highly desired and that even small improvements in drug purity are important improvements. This is due to the fact that impurities may have unanticipated impact on drug stability, safety, or efficacy. Accordingly, improved methods of purifying IGF-I/IGFBP-3 complexes are inherently useful and needed.

SUMMARY

In one embodiment, an isolated protein is produced which comprises a complex of insulin-like growth factor I ("IGF-I") and insulin-like growth factor binding protein 3 ("IGFBP-3"). The isolated protein can be at least about 96% pure, at least about 97% pure, at least about 98% pure, or at least about 99% pure.

In one embodiment, the complex comprises IGF-I and IGFBP-3 in a molar ratio from about 0.8:1 to about 1.2:1. In another embodiment, the molar ratio is about 1:1.

Pharmaceutical compositions are also provided which comprise an isolated protein comprising a complex of IGF-I and IGFBP-3 and a pharmaceutically acceptable carrier, where the protein is at least about 96%, at least about 97%, at least about 98%, or at least about 99% pure as measured by isocratic cation exchange methods described herein.

Methods of purifying a complex of IGF-I and IGFBP-3 are provided that comprise obtaining a complex of IGF-I and IGFBP-3, partially-purifying the IGF-I/IGFBP-3 complex, adsorbing the complex to a stationary phase, desorbing the complex using a multiplicity of mobile phases wherein the mobile phases comprise a series of sequentially increasing ionic strength, and recovering the purified IGF-I and IGFBP-3 complex. In one embodiment, the stationary phase is a cation exchange resin. In another embodiment, the cation exchange resin contains carboxymethyl functional groups. The rhIGF-I/rhIGFBP-3 complex is a charged protein complex, but subtle modifications to the protein complex can occur that reduce the charge of the complex by 1 to 5 positive units. This can be accomplished by neutralizing one or more positive charges or by introducing one or more negative charges. Examples of modifications that can change the overall charge in a positive charge manner include, but are not limited to, N-terminal amine conjugation, Lysine conjugate, Arginine conjugation, and deamidation. By establishing two isocratic buffer conditions, one can separate the native rhIGF-I/rhIGFBP-3 complex from that of a positive charge reduced rhIGF-I/rhIGFBP-3 complex. The first isocratic buffer has an ionic strength sufficient to desorb the positive charge reduced rhIGF-I/rhIGFBP-3 complex while retaining the native rhIGF-I/rhIGFBP-3 complex. The second isocratic buffer has an has an ionic strength sufficient to desorb the native rhIGF-I/rhIGFBP-3 complex while retaining other impurities such as aggregated rhIGF-I/rhIGFBP-3 and misfolded forms of rhIGFBP-3. FIG. 6 depicts two separations, the top figure using a preparative resin and the bottom using an analytical resin. The identity of the components is indicated above the UV trace for the peaks. Alternatively the method can be done with a single buffer that desorbs both the positive charge reduced rhIGF-I/rhIGFBP-3 complex and the native rhIGF-I/rhIGFBP-3 complex, with separation being achieved during the single isocratic buffer. This method is generally used for analytical analysis and is not generally used for preparative analysis due to the large volume of buffer required to achieve separation. Another alternative method can be done with a first isocratic buffer to desorb the positive charge reduced rhIGF-I/rhIGFBP-3 complex followed by a gradient of increasing ionic strength to elute the native rhIGF-I/rhIGFBP-3 complex and other impurities.

Methods are provided wherein the multiplicity of mobile phases comprise a first mobile phase and a second mobile phase. The first mobile phase can have a NaCl concentration at least about 20 mM less than the second mobile phase, at least about 30 mM less than the second mobile phase, or at least about 40 mM less than the second mobile phase, or at least about 50 mM less than the second mobile phase, or at least about 60 mM less than the second mobile phase. In another embodiment, the first mobile phase comprises about 160 mM to about 185 mM NaCl and the second mobile phase comprises about 200 mM to about 250 mM NaCl. The second mobile phase can also comprise about 225 mM NaCl. The choice of mobile phase is based largely upon the amount of positive charge reduced rhIGF-I/rhIGFBP-3 complex that is required to be removed to achieve the desired purity and the relative retention of the cation exchange resin.

Additionally, methods of purifying a partially-purified complex of IGF-I and IGFBP-3 are provided which comprise adsorbing the IGF-I/IGFBP-3 complex to a cation exchange resin and desorbing the complex using a stepwise series of mobile phases. In one embodiment, the mobile phases comprise a first mobile phase having from a sodium acetate buffering system at about pH 5.4-5.6 containing about 160 mM to about 185 mM NaCl and a second mobile phase having a sodium acetate buffering system at about pH 5.4-5.6 containing about 200 mM to about 250 mM NaCl. In another embodiment, the second mobile phase comprises about 225 mM NaCl.

In the methods of the present invention, the stepwise isocratic elution steps are employed using 5-15 column volumes of mobile phase per step. In one embodiment, the first isocratic step uses 5-10 column volumes of mobile phase.

Other objects, features and advantages of the present invention will become apparent from the following detailed description. The detailed description and specific examples are given for illustration only since various changes and modifications within the spirit and scope of the invention will become apparent to those skilled in the art from this detailed description. Further, the examples demonstrate the principle of the invention and cannot be expected to specifically illustrate the application of this invention to all the examples where it will be obviously useful to those skilled in the prior art.

BRIEF DESCRIPTION OF THE DRAWINGS

FIG. 7—(Top) Chromatogram of mass/variant #2 Pool and (Bottom) mass/variant #1 Pool by RP-HPLC.

FIG. 8—(Top) Summed spectra for IGFBP-3 peak for Mass/variant #2 Pool, (middle), Mass/variant #1 Pool, and (Bottom) and native rhIGF-I/rhIGFBP-3. The ion cluster corresponding to the +18 charge state of IGFBP-3 is shown.

FIG. 9—MaxEnt of the IGFBP-3 peak for Mass/variant #2 Pool. The mass/variant form of IGFBP-3 exhibits a mass of 28,988.

FIG. 10—MaxEnt of the IGFBP-3 peak for Mass/variant #1 Pool. The mass/variant of IGFBP-3 exhibits a mass of 28,909.

FIG. 11—Spectra of N-terminal peptide of IGFBP-3 for Mass/variant #1 Pool compared to rhIGF-I/rhIGFBP-3 Ref Std. The Mass/variant #1 Pool exhibits a Two observed IGFBP-3 N-terminal peptide masses. The mass/variant form of IGFBP-3 has an observed mass of 1608.7576 versus the unmodified peptide that exhibits a mass of 1502.6997 amu.

DETAILED DESCRIPTION

Complexes of IGF-I and IGFBP-3 with new levels of purity are provided. Chromatographic techniques have been developed that remove contaminants, such as mass and charge variants of IGFBP-3. The new techniques enable the production of high-quality pharmaceutical compositions comprising IGF-I/IGFBP-3 complexes.

Figure 1:
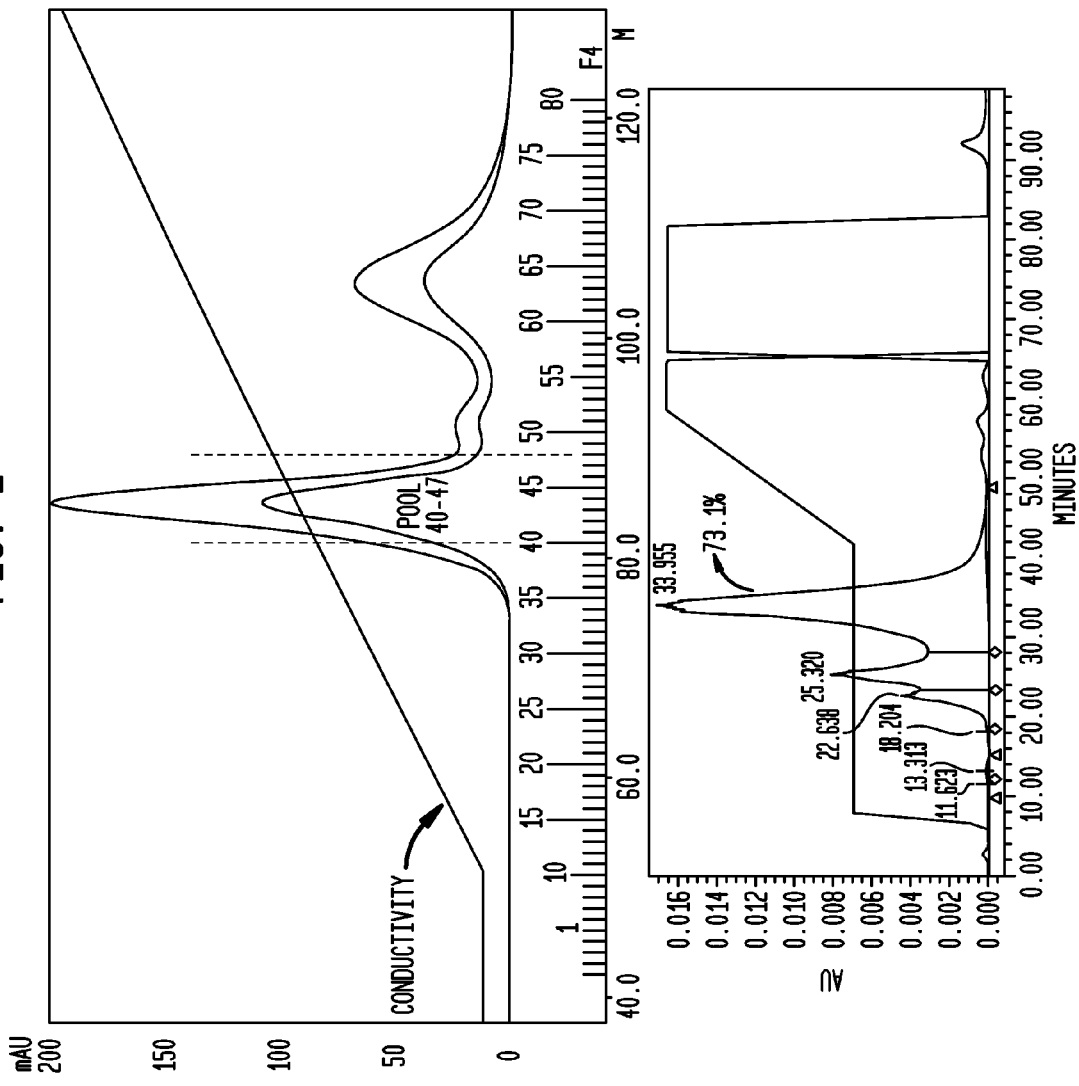
FIG. 1—(Top) Purification of partially purified rhIGF-I/rhIGFBP-3 using a ToyoPearl CM-650 resin with a linear gradient of NaCl. (Bottom) Analytical CM-HPLC analysis of the pooled fractions (40-47) from the linear purification. By this analysis the native rhIGF is 73.1% pure relative to other charge variant forms of the rhIGF-I/rhIGFBP-3 complex.
Figure 2:
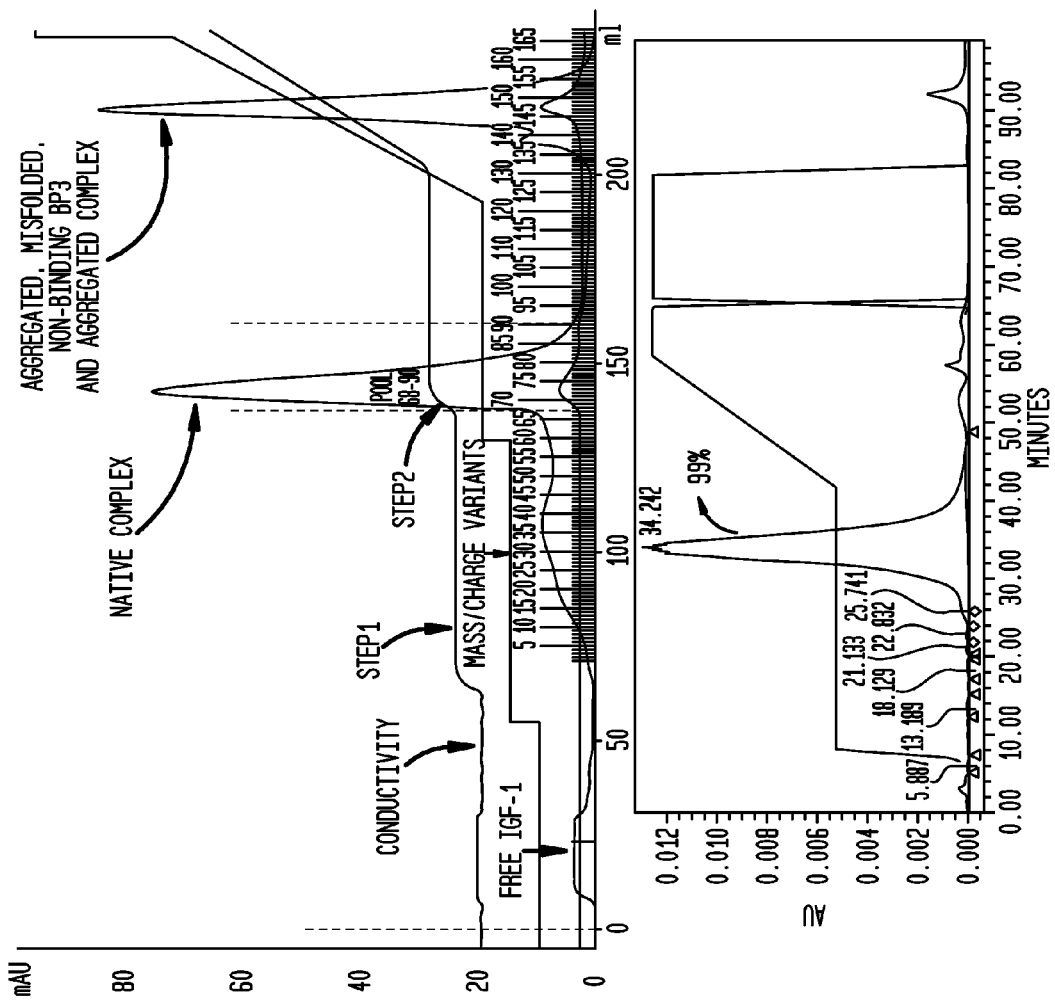
FIG. 2—(Top) Purification of partially purified rhIGF-I/rhIGFBP-3 using a ToyoPearl CM-650 resin with a stepwise isocratic elution of NaCl. (Bottom) Analytical CM-HPLC analysis of the pooled fractions (68-90) from the isocratic purification. By this analysis the native rhIGF is 99% pure relative to other charge variant forms of the rhIGF-I/rhIGFBP-3 complex.

It was surprisingly discovered that previous methods of manufacture yielded prior art compositions of partially-purified IGF-I/IGFBP-3 complexes contained mass and charge variants of IGFBP-3. FIG. 1 (Top) demonstrates the prior art method of purification of the rhIGF-I/rhIGFBP-3 complex using a linear gradient of NaCl to desorb the protein complex. FIG. 1 (bottom) shows an analysis of the pooled fractions from the linear gradient shown in FIG. 1 (top). As seen in FIG. 1 (bottom), several charge variant forms of the complex can be detected using an isocratic elution profile, the method of which is described herein. The overall purity of this material is only 73% comparing the native rhIGF-I/rhIGFBP-3 to that of other charge variant forms. Therefore linear gradient method of purification was not sufficiently robust to resolve minor charge form variants or the rhIGF-I/rhIGFBP-3 complex. Chromatographic methods for removing these variants and aggregates were developed. The new methods involve, for example, adsorbing a partially-purified IGF-I/IGFBP-3 complex to a cation exchange resin and desorbing the complex using a two-step elution technique. As seen in FIG. 2 (top) preparative isocratic of the partially-purified IGF-I/IGFBP-3 complexes results in an elution profile closely mimics the results observed using an analytical method. Pooled fractions from the peak that eluted during the $2^{nd}$ isocratic step (labeled Native Complex) provided a purity of 99% by the analytical CM method (shown in FIG. 2 (bottom).

DEFINITIONS

Unless otherwise limited by a specific recitation herein, the following terms have the following meanings:

"IGF-I" refers to insulin-like growth factor I, including, without limitation, naturally-occurring (i.e. "native") IGF-I, analogs or variants thereof, and fusions between IGF-I and other amino acid sequences.

"IGFBP-3" refers to human insulin-like growth factor binding protein 3. Herein, IGFBP-3 can also refer to IGFBP-3 analogs, naturally-occurring allelic variants, and fusions between IGFBP-3 and other amino acid sequences.

"Complex" refers to a group of two or more associated proteins. Proteins in a complex associate through any of a multiplicity of non-covalent interactions including, without limitation, ionic bonds, hydrogen bonds, van der waals forces, and hydrophobic interactions. IGF-I and IGFBP-3 are present in a complex in various molar ratios. A complex can comprise IGF-I and IGFBP-3 in a molar ratio of about 0.8:1 to about 1.2:1. In addition, a complex can comprise IGF-I and IGFBP-3 in a molar ratio of about 1:1.

"Partially-purified" refers to a complex of IGF-I and IGFBP-3 which has, to some extent, been freed of cellular or fermentation contaminants, and/or concentrated, and/or desalted. "Partially-purified" also refers to a complex of IGF-I and IGFBP-3 which has undergone one or more previous purification steps, including, without exclusion, such techniques as size exclusion chromatography, hydrophobic interaction chromatography, or ion exchange purification. "Partially-purifying" refers to subjecting a complex of IGF-I and IGFBP-3 to one or more purification steps. "Partially-purified" also refers to a complex of IGF-I and IGFBP-3 with is substantially purified but requires "polishing" to remove aggregated forms of rhIGF-I/rhIGFBP-3, misfolded IGFBP-3, or mass/charge variant forms of the rhIGF-I/rhIGFBP-3 complex.

"Preparative chromatography" refers to the preparation of pure or partially-pure products on a technical scale.

"Gradient elution or Linear elution" refers to the practice of continually changing the composition of the mobile phase over the entire chromatographic analysis.

"Isocratic elution" and "isocratically" refer to the practice of maintaining the constituents of the mobile phase constant over a period of time.

"Mobile phase" refers to aqueous solutions of specified buffering capacity and ionic strength. Pharmaceutically acceptable buffering salts are employed in the manufacture of rhIGF-I/rhIGFBP-3. Pharmaceutically acceptable cations, such as sodium are used to affect the ionic strength. The mobile phase can incorporate water miscible solvents.

"Stationary phase" refers to organic polymeric chromatography materials which are effective to bind (i.e., adsorb) an analyte under selected mobile phase conditions and to release the analyte under other selected mobile phase conditions.

"Organic polymeric chromatography materials" includes cation exchange resins. These materials include weak cation exchange resins and resins possessing carboxylate functional groups. "Carboxylate functional groups" are exemplified by, for instance, carboxyl and carboxymethyl compounds.

"Step elution" and "stepwise elution" refer to the practice of changing the mobile phase conditions from one isocratic mobile phase to a second isocratic mobile phase, typically with increasing ionic strength between each step. Elution (or desorption) of the protein of interest is achieved by selecting an isocratic mobile phase that selectively desorbs the protein during the isocratic step.

Discussion

Complexes of IGF-I and IGFBP-3 are isolated to new levels of purity using chromatographic techniques designed to remove both mass and charge variants of IGFBP-3 and IGF-I/IGFBP-3 complex aggregates. These chromatographic techniques are suitable for analytical, for semi-preparative, and for preparative chromatography.

A method of purifying a complex of IGF-I and IGFBP-3 comprises obtaining a complex of IGF-I and IGFBP-3, partially-purifying the complex, adsorbing the complex to a stationary phase, desorbing the complex using a multiplicity of mobile phases wherein the mobile phases are a series of sequentially increasing ionic strength, and recovering the purified complex.

In addition, a method of purifying a partially-purified complex of IGF-I and IGFBP-3 comprises adsorbing the complex of IGF-I and IGFBP-3 to a stationary phase and desorbing the complex using a step-wise series of mobile phases, thereby obtaining the purified complex.

In another embodiment, a method of purifying a partially-purified complex of IGF-I and IGFBP-3 by ion exchange chromatography using a carboxymethyl resin the improvement comprising desorbing said complex from the carboxymethyl resin by the application of a first mobile phase comprising from about 160 mM to about 185 mM NaCl followed by the application of a second mobile phase comprising from about 200 mM to about 250 mM NaCl, thereby recovering a purified complex of IGF-I and IGFBP-3 in the second mobile phase.

Such techniques use a variety of stationary phases. Useful stationary phases include organic polymeric chromatography materials such as cation exchange resins. Useful stationary phases also include weak cation exchange resins possessing carboxylate functional groups, such as carboxymethyl functional groups.

These techniques also use a variety of mobile phases. These chromatographic techniques use at least two mobile phases, but may employ as many mobile phases which are necessary to obtain a purified analyte or a plurality of purified analytes of interest. Mobile phases consist of various ionic strength which are each applied to the stationary phase in a stepwise fashion (as opposed to application in a gradient) as is sometimes known to those skilled in the art as "step elution." Likewise after obtaining the purified analyte or analytes, stepwise application is unnecessary and, for instance, a gradient up to a high salt concentration may be used to clean, clear or regenerate the stationary phase. Alternatively, the application of a single mobile phase of high salt concentration, such as 1 M NaCl, after obtaining the purified analyte can also clean, clear or regenerate the stationary phase.

Mobile phase density can be varied by adjusting the aqueous solutions salt concentration. Useful mobile phases have a NaCl concentration of at least about 60 mM less than an immediately subsequent second mobile phase. Mobile phases also have NaCl concentrations of at least about 50 mM less than an immediately subsequent second mobile phase, or at least about 40 mM less than an immediately subsequent second mobile phase or at least about 30 mM less than an immediately subsequent second mobile phase, or at least about 20 mM less than an immediately subsequent second mobile phase or at least about 10 mM less than an immediately subsequent second mobile phase. For preparative cation resin, the first mobile phases have from about 160 mM to about 185 mM NaCl. The second mobile phases can be applied to the stationary phase immediately subsequent to the first mobile phases. For preparative cation resins Second mobile phases can have from about 200 mM to about 250 mM NaCl. Second mobile phases can also have about 225 mM NaCl.

These methods produce pure proteins comprising complexes of IGF-I and IGFBP-3. The complexes of IGF-I and IGFBP-3 can be at least about 96% pure. The complexes can also be at least about 97% pure, at least about 98% pure, or at least about 99% pure. An isolated protein can comprise complexes of IGF-I and IGFBP-3 in a molar ratio of about 0.8:1 to about 1.2:1. In addition, an isolated protein can comprise complexes of IGF-I and IGFBP-3 in a molar ratio of about 1:1.

These isolated proteins are useful for the treatment of the disorders disclosed, for example, in U.S. Pat. Nos. 5,681,818, 5,723,441, 5,948,757, 6,015,786, 6,017,885, 6,025,332, 6,025,368, 6,514,937, and 6,518,238. A pharmaceutical composition can comprise an isolated protein comprising a complex of IGF-I and IGFBP-3 and a pharmaceutically acceptable carrier, wherein the protein is at least about 96% pure. In other embodiments, the pharmaceutical composition can have a protein at least about 97% pure, at least about 98% pure, or at least about 99% pure. A pharmaceutical composition can comprise an isolated protein of complexes of IGF-I and IGFBP-3 in a molar ratio of about 0.8:1 to about 1.2:1. In addition, a pharmaceutical composition can comprise an isolated protein of complexes of IGF-I and IGFBP-3 in a molar ratio of about 1:1.

EXAMPLES

The following examples are illustrative of the present invention and are not intended to be limitations thereon.

Example #1

Purification Methods

Preparative CM Purification

Figure 3:
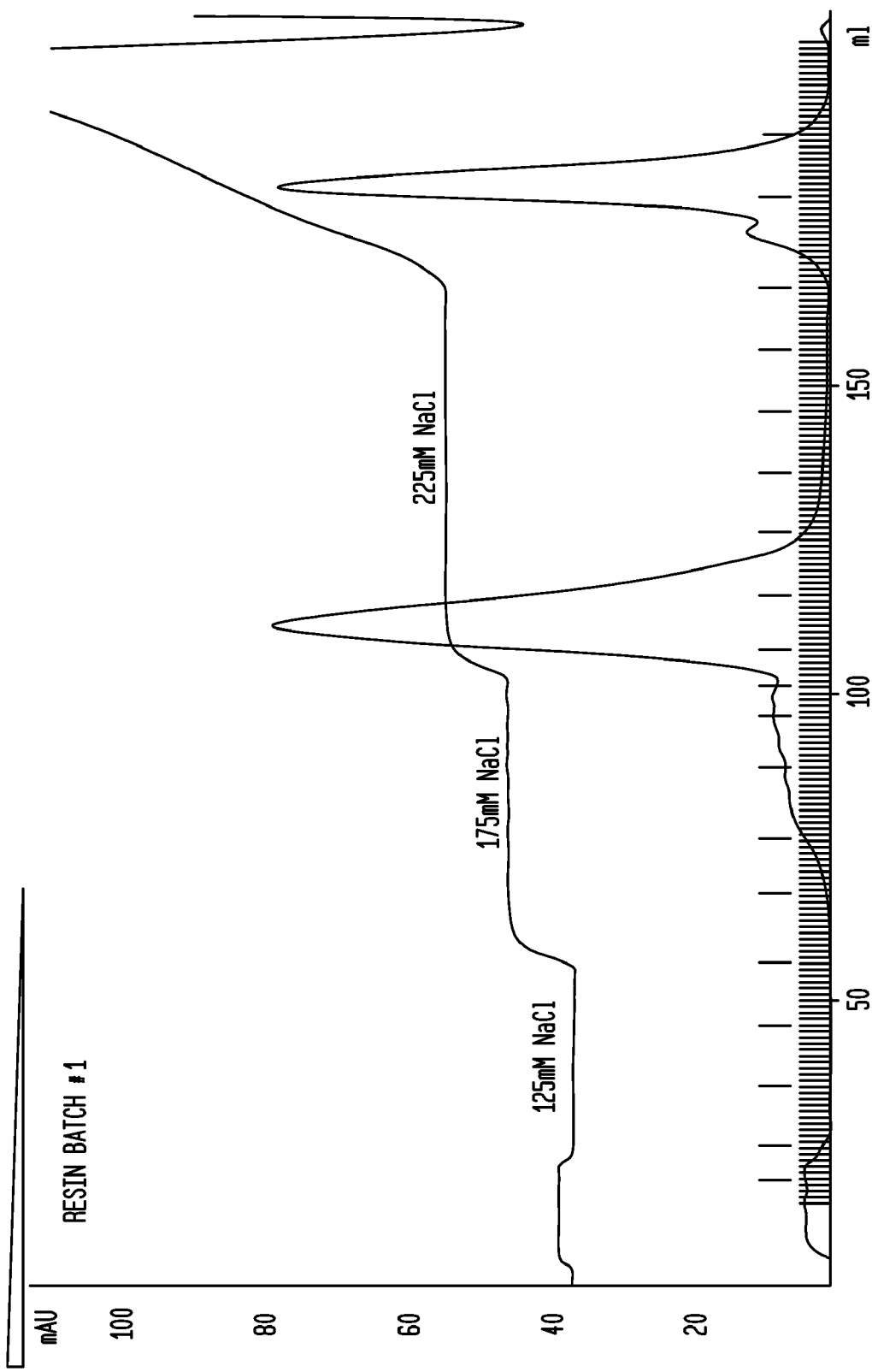
FIG. 3—Purification of partially purified rhIGF-I/rhIGFBP-3 using a ToyoPearl CM-650 resin (Batch #1) with a stepwise isocratic elution 175 mM and 225 mM NaCl.
Figure 4:
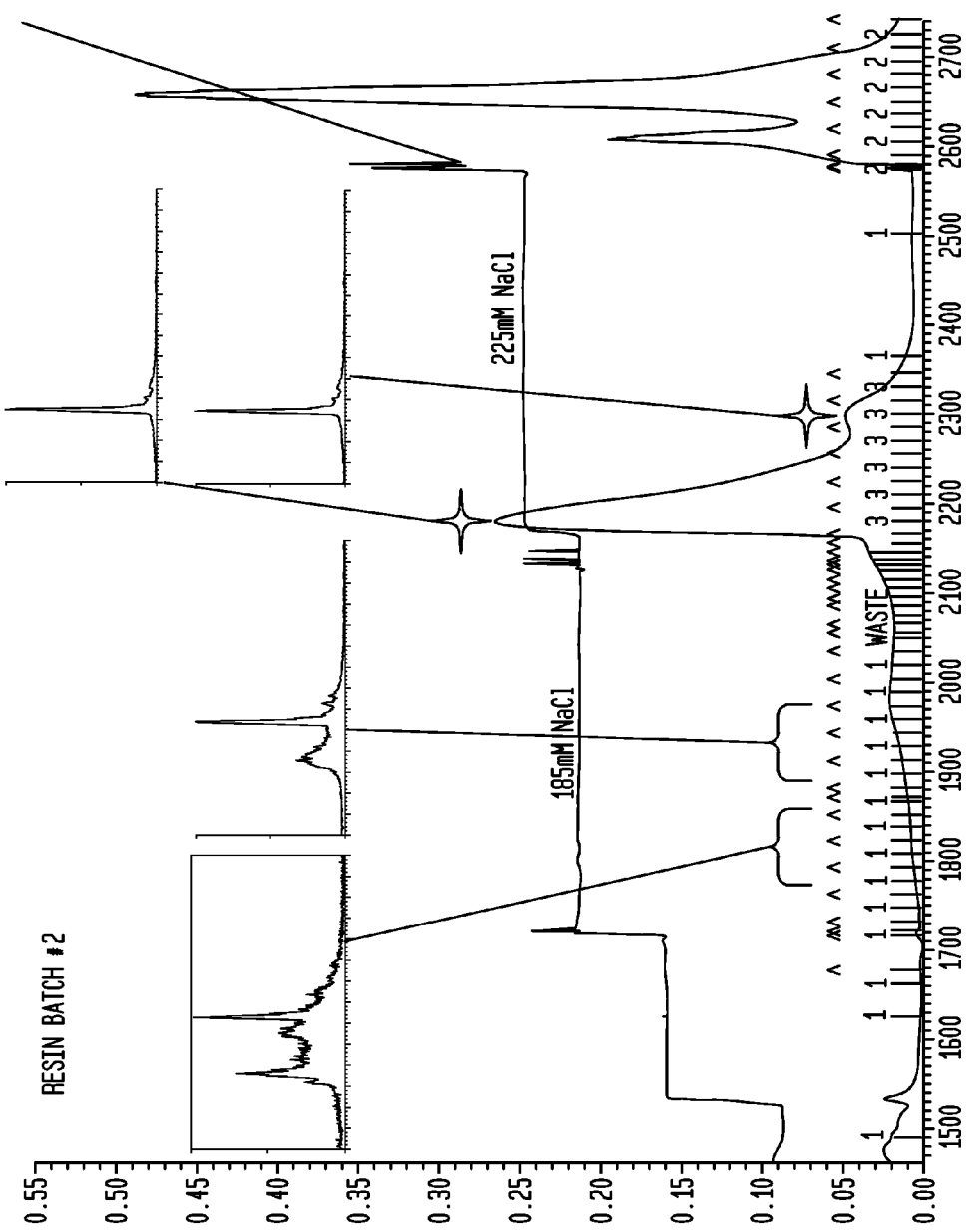
FIG. 4—Purification of partially purified rhIGF-I/rhIGFBP-3 using a ToyoPearl CM-650 resin (Batch #2) with a stepwise isocratic elution 185 mM and 225 mM NaCl. Inset balloons are mass spectrophotometer analysis of an ion cluster of IGFBP-3 found in the pooled fractions. See also FIG. 8.
Figure 5:
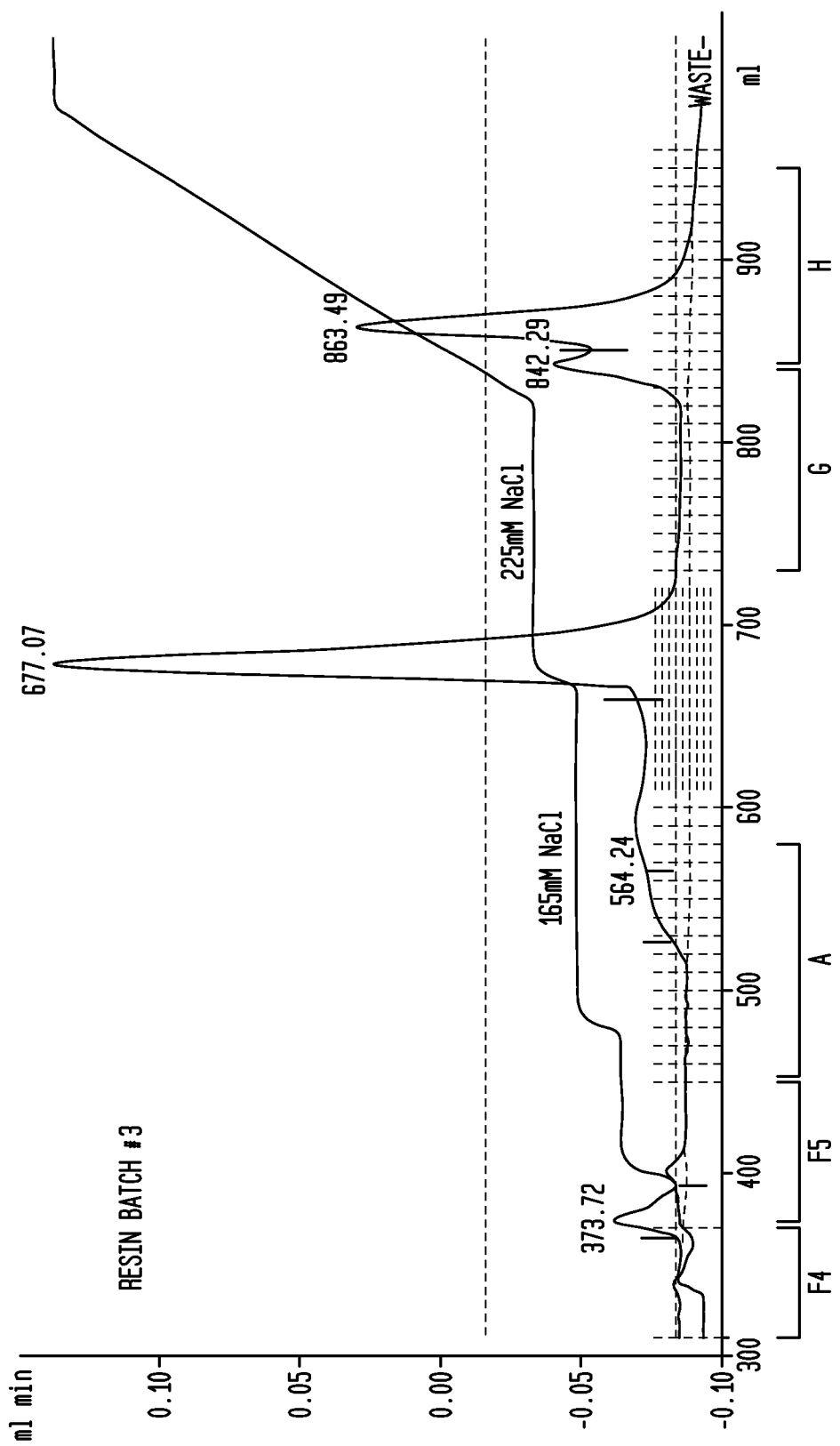
FIG. 5—Purification of partially purified rhIGF-I/rhIGFBP-3 using a ToyoPearl CM-650 resin (Batch #3) with a stepwise isocratic elution 165 mM and 225 mM NaCl.

Experiments were conducted using three manufacturer resin lots of Toyopearl™ CM-650M resin (Tosoh Bioscience LLC, Montgomeryville, Pa., Catalog No. 14696). The general procedure for chromatography is defined below. The ionic strength of the $1^{st}$ isocratic elution buffer was tailored to achieve the desired separation profile. Preparative chromatograms are shown in FIGS. 3, 4, and 5.
Loading buffer—50 mM sodium acetate, 50 mM NaCl, pH 5.5
Washing buffer—50 mM sodium acetate, 125 mM NaCl, pH 5.5
$1^{st}$ isocratic buffer—50 mM sodium acetate, 165-185 mM NaCl, pH 5.5
$2^{nd}$ isocratic buffer—50 mM sodium acetate, 225 mM NaCl, pH 5.5
Gradient—50 mM sodium acetate, 225 mM NaCl, pH 5.5 mixture to 1M NaCl The $1^{st}$ isocratic step was applied for 6-9.5CV depending on the run. The $2^{nd}$ isocratic step was applied until the native rhIGF-I/rhIGFBP-3 peak returned within 5% of baseline absorbance. The gradient between 225 mM NaCl and 1M NaCl was conducted to regenerate the resin.

Resin lot#1 required 175 mM NaCl to elute the mass/charge variant forms or the rhIGF-I/rhIGFBP-3 complex. Resin lot #2 required 185 mM NaCl to elute the mass/charge variant forms or the rhIGF-I/rhIGFBP-3 complex. Resin lot #3 required 165 mM NaCl to elute the mass/charge variant forms or the rhIGF-I/rhIGFBP-3 complex.

All lots efficiently desorbed the native rhIGF-I/rhIGFBP-3 complex at 225 mM NaCl in a desired minimum volume. Moreover, none of the impurities that eluted during the salt gradient eluted during the 225 mM NaCl step in any of the 3 resin batches.
Analytical CM-HPLC
Reagents
Column: Tosoh Biosep TSK Gel CM-5PW, 10μ, 100 Å, 7.5 mm×7.5 cm, (Part No. 13068)
 Solvent A=50 mM Sodium Acetate/50 mM Sodium Chloride pH 5.5
  27.2 g Sodium acetate+11.69 g Sodium chloride+4 L Water, pH 5.5
 Solvent B=50 mM Sodium Acetate/550 mM Sodium Chloride pH 5.5
  27.2 g Sodium acetate+128.6 g Sodium chloride+4 L Water, pH5.5
 Solvent C=50 mM Sodium Acetate/1000 mM Sodium Chloride pH 5.5
  27.2 g Sodium acetate+233.76 g Sodium chloride+4 L Water, pH 5.5

Buffers are prepared by first adding the prescribed amount of salts to water and mixing until dissolved. The pH is then adjusted to 5.5-5.6 using acetic acid. After a stable pH is obtained, the solution is brought to volume with water and the pH is confirmed. All solutions are filtered using 0.22μ or 0.45μ filter prior to use.
LC conditions
Detector
 Wavelength=276 nm
 AUFS=2
 Time constant=1
Pump
 Flow rate=1 ml/min
 Solvent A=50 mM Sodium Acetate, 50 mM NaCl pH 5.5
 Solvent B=50 mM Sodium Acetate, 550 mM NaCl pH 5.5
 Solvent C=50 mM Sodium Acetate, 1000 mM NaCl pH 5.5
 Solvent D=Water
Gradient Chart: Column #2 (Lot # F0045-101C)

| Step | Time | Flow | % A | % B | % C | % D | Curve |
|---|---|---|---|---|---|---|---|
| 1 | 0 | 1 | 100 | | | | |
| 2 | 7.0 | 1 | 100 | | | | 6 |
| 3 | 7.1 | 1 | 57 | 43 | | | 6 |
| 4 | 42.0 | 1 | 57 | 43 | | | 6 |
| 5 | 58.5 | 1 | | 100 | | | 6 |
| 6 | 65.0 | 1 | | 100 | | | 6 |
| 7 | 66.0 | 1 | | | 100 | | 6 |
| 8 | 82.5 | 1 | | | 100 | | 6 |
| 9 | 83.0 | 1 | 100 | | | | |
| 10 | 99.0 | 1 | 100 | | | | |

Figure 6:
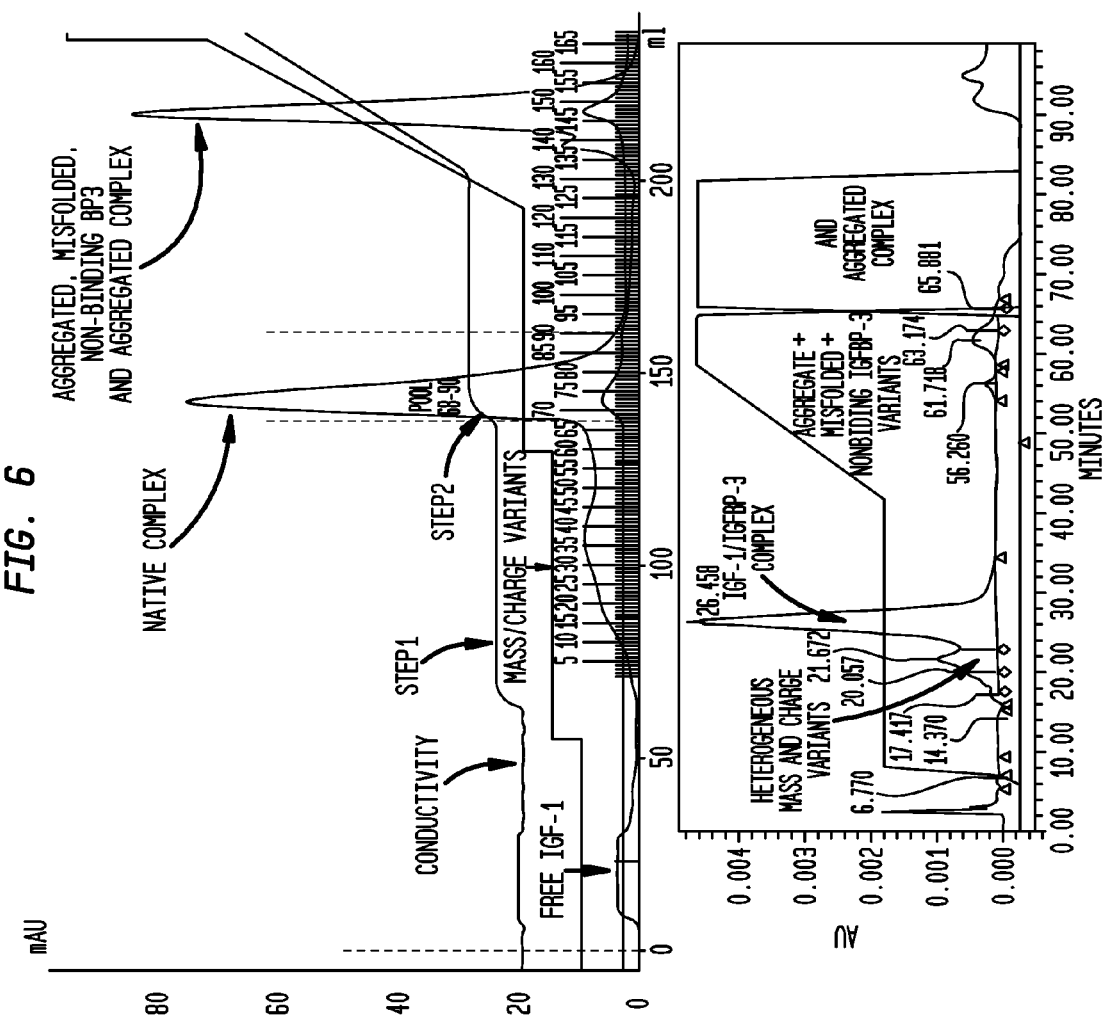
FIG. 6—Comparison of the elution profiles observed using a preparative CM resin (ToyoPearl CM-650) compared to an analytical CM resin (Tosho BioSep TSK Gel CM-5PW).

Note—the ratio of buffer A to buffer B during steps 3 and 4 are adjusted based on the retention properties of the column lot such that the retention time of the native IGF-I/IGFBP-3 elutes between 30.0 and 41.0 minutes. If mass variant peaks are present in the sample they will elute prior to the rhIGF-I/rhIGFBP-3 peak during the isocratic step.
Comparison Between Analytical CM Separation and Preparative CM Separation FIG. 6 (bottom) shows a chromatogram of an analytical CM-HPLC run with the peaks identified as their components. As can be seen by comparing the preparative CM separation (top) to that of the analytical CM (bottom) it will be appreciated that the same components elute in the same order of retention and can be identified on this basis.

FIG. 1 (bottom) and FIG. 2 (bottom) show results of analytical CM-HPLC for samples containing mass/charge variant forms of the rhIGF-1/rhIGFBP-3 complex (FIG. 1), and a sample containing little mass/charge variant forms of the rhIGF-I/rhIGFBP-3 complex (FIG. 2).

Example #2

Characterization of Mass/Charge Variant Forms of rhIGF-I/rhIGFBP-3

C18 Reverse Phase HPLC (Vydac Method)+/−MS Detection LC Conditions

| Column | Vydac 218 TP54 reverse phase C18 4.6 × 250 mm id |
|---|---|
| Eluent A | 50% Acetonitrile, 0.1% TFA |

-continued

| | |
|---|---|
| Eluent B | 0.1% TFA |
| Eluent C | 100% Acetonitrile, 0.1% TFA |
| Flow Rate | 0.9 ml/min |
| Injection Volume | up to 100 u |
| Column Temperature | Ambient |
| Detection Wavelength | 210 nm |
| Run Time | 95 minutes |

Gradient Table

| Time min | Flow | % A | % B | % C | Change |
|---|---|---|---|---|---|
| 0 | 0.9 | 10 | 90 | | — |
| 8 | 0.9 | 10 | 90 | | 6 |
| 25 | 0.9 | 52 | 48 | | 6 |
| 55 | 0.9 | 68 | 32 | | 6 |
| 60 | 0.9 | 100 | | | 6 |
| 70 | 0.9 | | | 100 | 6 |
| 80 | 0.9 | | | 100 | 6 |
| 85 | 0.9 | 10 | 90 | | 6 |
| 95 | 0.9 | 10 | 90 | | 6 |

LCMS analyses were performed using a Waters Alliance 2695 HPLC system coupled to a MicroMass LCT (TOF) mass spectrometer and a Waters 2996 photodiode array (PDA) detector. The chromatographic separation was accomplished using a Vydac 218TP (250×4.6 mm, 300 A) C18 reverse phase column eluting with a H2O-acetonitrile gradient containing 0.1% (v/v) trifluoroacetic acid (TFA). The eluent stream from the reverse phase column was split (4 to 1), with the larger portion of the stream directed to the PDA detector and the remainder to the electrospray source.

LCMS of AspN Peptide Map

Samples of the mass/charge variant#1 Pool were analyzed by peptide digestion followed by RP-LC/MS analysis.

The proteolytic fragments were separated using a Cadenza (Cat# CD026) 1 um (2×250 mm) C18 RP-HPLC column at a flow rate of 0.2 ml/min over a range from 2% acetonitrile to 98% acetonitrile. Peaks were detected using absorbance of the eluate stream at 210 nm from a photodiode array detector, which was then infused into a MicroMass LCT mass spectrometer operating in the positive ion electrospray ionization mode. The peptide peak pattern (i.e. the peptide map) was compared to a reference standard to establish identity. Subsequently the peaks were identified by summing the total ion current under each peak and measuring monoisotopic, M2+, or M3+ ions.

Samples and Injection Parameters

In-process samples were pulled during the course of a manufacturing campaign. The samples were frozen and stored at −20° C. until analysis.

Isocratic Wash Step Impurities

Samples were taken during the isocratic wash step prior to elution of the native complex from the run shown in FIG. 4. Samples representing two broad peaks that eluted during this were step were pooled. Equal volumes of each fraction were combined to form the pool and the pools were concentrated using 10 kD ultrafiltration membranes (Centricon YM-10; Amicon cat #4206).

For the basis of comparison, a fraction was also taken from the top of the peak during elution of the native rhIGF-I/rhIGFBP-3 complex during the 225 mM isocratic elution step. A sample was also take from a shoulder of the 225 mM isocratic peak (which was caused by a short-term flux in the conductivity during the step.) of the buffer.

These samples were used for analysis by LCMS and one sample was analyzed by peptide mapping.

Results for Iscocratic Wash Step Impurity Samples
RP-HPLC with MS Characterization FIG. 7 shows chromatograms of Mass/variant #2 Pool and Mass/Variant #1 Pool measured by Vydac RP-HPLC. In FIG. 1, the native IGF-I elutes as a peak at 41.8-42 minutes, with oxidized IGF-I eluting immediately prior to the native IGF-I peak. The IGFBP-3 elutes as a peak at 48-48.7 minutes. There are no other significant impurities observed in these samples.

The spectra was summed over the peak for IGFBP-3 in each of these samples as well as that of a sample representing the apex of the 225 mM NaCl isocratic step. FIG. 8 shows expansions of the mass spectra summed across the IGFBP-3 peak for, and native rhIGF-I/rhIGFBP-3 around m/z 1597, corresponding to the +18 charge state of the IGFBP-3 ion cluster. This demonstrates that IGFBP-3 is significantly modified in the Mass/variant #2 Pool and Mass/variant #2 Pool samples, but relatively little of the IGFBP-3 in the 225 mM salt elution peak is modified. As a note, these are the same spectra shown as balloons in FIG. 4. There are numerous modifications seen in the Mass/variant #2 Pool sample, but a prominent ion is seen at 1611.3 amu. FIG. 9 shows the MaxEnt spectra of this sample, which indicates a protein with a molecular weight of 28988.5313, which is +257.03 relative to the calculated mass of rhIGFBP-3 (28731.5). There are numerous modifications seen in the Mass/variant #1 Pool sample, but a prominent ion is seen at 1606.9 amu. FIG. 10 shows the MaxEnt spectra of this sample, which indicates a protein with a molecular weight of 28909.5547, which is +178.05 relative to the calculated mass of rhIGFBP-3

Peptide Mapping of Mass/Variant #1 Pool

The UV chromatogram of the AspN peptide of Mass/variant #1 Pool compared to rhIGF-I/rhIGFBP-3 reference standard were compared and there were no distinct appearance or disappearance of any prominent peaks. Therefore the mass variants observed did not result in distinctly different migration of any of the peaks.

Spectra were summed over the region of the chromatogram near the peaks at 46.1-46.5 minutes, corresponding to the retention time of the N-terminal peptide for rhIGFBP-3. FIG. 11 shows the monoisotopic ion clusters corresponding to the peptide at the N-terminus of IGFBP-3 for (top) and the rhIGF-I/rhIGFBP-3 reference standard (bottom). The Mass/variant #1 Pool sample exhibits an ion cluster at 1502.6997 that corresponds to that of native N-terminal peptide of IGFBP-3 as well as an ion cluster at 1680.7576, which is +178.0579 compared to the parent peptide. This observed mass adduct is consistent with the mass adduct calculated for the whole protein by MaxEnt (+178.05). Thus this single mass adduct addition would account for the modification to the IGFBP-3. The 1680.7576 peptide is not present in the reference standard as seen by comparing the top ion cluster trace to the bottom ion cluster trace due to lack of sensitivity of the peptide mapping method.

Identity of IGFBP-3 Mass Variants

In expanded spectra around the +18 charge state of IGFBP-3, the most prominent ions observed samples were at 1611.3 (Mass/variant #2 Pool) and 1606.9 (Mass/variant #1 Pool) corresponding to the mass adducts of approximately 258 and 178 amu respectively.

The peptide sequence of this peptide is *GASSAGLGPV-VRCEPC (SEQ ID NO: 1), with the 1st glycine residue representing the N-terminus of IGFBP-3. The calculated monoisotopic mass of this peptide is 1502.7090.

Potential modifications that could account for mass adducts at 178 and 258 amu were considered. The most likely possibility is N-terminal gluconylation (178 amu) and N-terminal alpha-N-6-phosphogluconylation (258 amu). Geoghegan et al report modification of an *E. coli* expressed protein with an N-terminal sequence of GSS[His]6 (SEQ ID NO: 2) in which the N-terminal glycine residue is subject of modification (Geoghegan et al (1999) Anal. Biochem 267(1) 169-84).

N-terminal gluconylation would conjugate a $C_6H_{10}O_6$ (178.0477 amu) moiety onto the peptide to an amine group. The mass of the observed modification is 1680.7576−1502.6997=178.0579 amu. Thus the observed adduct is consistent with this modification (178.0477−178.0579=−0.0102 amu) which is within experimental error and the limits of this mass spectrometer. There are two possible sites of modification, the N-terminal amine group on the Glycine residue and the guanidinyl group on the Arginine.

Example #3

Analytical CM-HPLC of Historical Manufacturing Lots of rhIGF-I/rhIGFBP-3

Charge variants of rhIGFBP-3 are detected by separation of mass/charge variant forms of rhIGF-1/rhIGFBP-3 complex using an isocratic gradient of sodium chloride on a TSK-GEL CM-5PW ion exchange column, 7.5 cm×7.5 mm ID, 10 um, according to the test method described supra.

These impurities were not previously detected in Drug Product lots with the methods that were available at the time of their manufacture. Where available, samples were obtained from retains to establish a range of these impurities in the historical samples. The results shown in Table 1 are reported as purity of the native rhIGF I/rhIGFBP-3, with the difference being associated with two peaks representing two mass/charge variants. The highest degree of purity observed was 95.4% by this method.

TABLE 1

Analysis of rhIGF-I/rhIGFBP-3 Mass/Charge Variants in Historical Drug Product Lots

| Drug Product Lot | Variant 2 (% Area) | Variant 1 (% Area) | rhIGF-I/rhIGFB-3 (% Area) |
|---|---|---|---|
| #1 | 1.7 | 5.3 | 93.1 |
| #2 | 0.6 | 6.3 | 93.1 |
| #3 | 1 | 7.2 | 91.8 |
| #4 | 0.7 | 5.3 | 94 |
| #5 | 0.4 | 5.9 | 93.6 |
| #6 | 0.2 | 4.3 | 95.4 |
| #7 | 0.5 | 5.2 | 94.2 |
| #8 | 0.4 | 5.2 | 94.3 |

The invention has been disclosed broadly and illustrated in reference to representative embodiments described above. Those skilled in the art will recognize that various modifications can be made to the present invention without departing from the spirit and scope thereof.

What is claimed is:

1. An isolated protein complex comprising insulin-like growth factor I (IGF-I) and insulin-like growth factor binding protein 3 (IGFBP-3), wherein said protein complex is at least 96% free of mass and charge variants as measured by analytical CM-HPLC.

2. The protein complex of claim 1, wherein said protein complex is at least 97% free of mass and charge variant as measured by analytical CM-HPLC.

3. The protein complex of claim 1, wherein said protein complex is at least 98% free of mass and charge variants as measured by analytical CM-HPLC.

4. The protein complex of claim 1, wherein said protein complex is at least 99% free of mass and charge variants as measured by analytical CM-HPLC.

5. The protein complex of claim 1, wherein said protein complex comprises IGF-I and IGFBP-3 in a molar ratio from about 0.8:1 to about 1.2:1.

6. The protein complex of claim 1, wherein said protein complex comprises IGF-I and IGFBP-3 in a molar ratio of about 1:1.

7. A pharmaceutical composition comprising an isolated protein complex comprising insulin-like growth factor I (IGF-I) and insulin-like growth factor binding protein 3 (IGFBP-3) and a pharmaceutically acceptable carrier, wherein said protein complex is at least 96% free of mass and charge variants as measured by analytical CM-HPLC.

8. The pharmaceutical composition of claim 7, wherein said protein complex is at least 97% free of mass and charge variants as measured by analytical CM-HPLC.

9. The pharmaceutical composition of claim 7, wherein said protein complex is at least 98% free of mass and charge variants as measured by analytical CM-HPLC.

10. The pharmaceutical composition of claim 7, wherein said protein complex is at least 99% free of mass and charge variants as measured by analytical CM-HPLC.

* * * * *

SEQUENCE LISTING

```
<160> NUMBER OF SEQ ID NOS: 2

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Ala Ser Ser Ala Gly Leu Gly Pro Val Val Arg Cys Glu Pro Cys
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Ser Ser His His His His His His
1               5
```